United States Patent
Koguma et al.

(10) Patent No.: US 9,643,174 B2
(45) Date of Patent: May 9, 2017

(54) TEMPERATURE RESPONSIVE ADSORBENT HAVING A STRONG CATION EXCHANGE GROUP AND METHOD FOR PRODUCING THE SAME

(71) Applicant: ASAHI KASEI MEDICAL CO., LTD., Tokyo (JP)

(72) Inventors: Ichiro Koguma, Chiyoda-ku (JP); Hiroki Shigematsu, Chiyoda-ku (JP); Kazuo Okuyama, Chiyoda-ku (JP); Teruo Okano, Shinjuku-ku (JP); Yoshikatsu Akiyama, Shinjuku-ku (JP); Kenichi Nagase, Shinjuku-ku (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/542,686

(22) Filed: Nov. 17, 2014

(65) Prior Publication Data

US 2015/0080484 A1 Mar. 19, 2015

Related U.S. Application Data

(62) Division of application No. 13/994,255, filed as application No. PCT/JP2011/079392 on Dec. 19, 2011.

(30) Foreign Application Priority Data

Dec. 17, 2010 (JP) ................................. 2010-282373

(51) Int. Cl.
*B01J 39/20* (2006.01)
*C07K 1/18* (2006.01)
(Continued)

(52) U.S. Cl.
CPC ............. *B01J 39/20* (2013.01); *B01J 20/285* (2013.01); *B01J 20/3276* (2013.01);
(Continued)

(58) Field of Classification Search
USPC ....................................... 521/33, 38
See application file for complete search history.

(56) References Cited

U.S. PATENT DOCUMENTS 3,549,016 A * 12/1970 Rigopulos .......... B01D 67/0011
210/500.33
6,706,187 B1 3/2004 Okano et al.
(Continued)

FOREIGN PATENT DOCUMENTS

| CA | 2737404 A1 | | 3/2010 |
| CN | 101781386 | * | 7/2010 |

(Continued)

OTHER PUBLICATIONS

Mitsuru Higa et al., "Design and Preparation of a Novel Temperature-Responsive Ionic Gel. 1. A Fast and Reversible Temperature Response in the Charge Density", J. Phys. Chem. B., vol. 108, pp. 16703-16707 (2004).*

(Continued)

*Primary Examiner* — Mark Kaucher
*Assistant Examiner* — Henry Hu
(74) *Attorney, Agent, or Firm* — Greenblum & Bernstein, P.L.C.

(57) ABSTRACT

Provided is a temperature responsive adsorbent prepared by immobilizing a copolymer containing at least N-isopropylacrylamide to a base material surface. The copolymer has at least a strong cation exchange group. In addition, the copolymer contains the strong cation exchange group in an amount of 0.01 to 5 mol % relative to N-isopropylacrylamide in terms of monomer.

7 Claims, 2 Drawing Sheets

| | Content of starting vinyl sulfonic acid mol% | Sulfonic acid group-containing monomer unit mol% | Elution amount of antibody by temperature change (A) mg/mL | Elution amount of antibody by a salt buffer (B) mg/mL | A/(A+B) × 100 % |
|---|---|---|---|---|---|
| Example 7 | 2 | 0.7 | 30.1 | 1.1 | 96.5 |

(51) Int. Cl.
- *B01J 39/26* (2006.01)
- *C08F 293/00* (2006.01)
- *B01J 20/285* (2006.01)
- *B01J 20/32* (2006.01)
- *B01J 39/05* (2017.01)
- *B01J 39/19* (2017.01)

(52) U.S. Cl.
CPC ........... *B01J 20/3278* (2013.01); *B01J 39/05* (2017.01); *B01J 39/19* (2017.01); *B01J 39/26* (2013.01); *C07K 1/18* (2013.01); *C08F 293/005* (2013.01); *C08F 2438/01* (2013.01)

(56) References Cited

U.S. PATENT DOCUMENTS

| | | | |
|---|---|---|---|
| 2004/0134846 A1 | 7/2004 | Akiyama et al. | |
| 2004/0203149 A1* | 10/2004 | Childs | B01D 67/0006 435/404 |
| 2007/0163332 A1 | 7/2007 | Tsujii et al. | |

FOREIGN PATENT DOCUMENTS

| | | | |
|---|---|---|---|
| CN | 101781386 A | | 7/2010 |
| CN | 101870793 | * | 10/2010 |
| CN | 101870793 A | | 10/2010 |
| JP | 2003-183569 A | * | 7/2003 |
| JP | 2004-137294 A | * | 5/2004 |
| JP | 2004-331776 | | 11/2004 |
| JP | 2006-519273 | * | 8/2006 |
| JP | 2007-69193 | | 3/2007 |
| JP | 2009-85933 | | 4/2009 |
| JP | 2012/081727 | | 6/2012 |
| WO | 99/061904 | | 12/1999 |
| WO | 01/074482 | | 10/2001 |
| WO | WO-2012/081727 A1 | * | 6/2012 |

OTHER PUBLICATIONS

Nagase et al., Polymer Preprints, Japan, vol. 58, No. 2, pp. 5116-5117 (2009).*
Polymer Preprints, Japan, 2009, pp. vol. 58, No. 2, 3T1-13.
Mitsuru Higa et al., "Design and Preparation of a Novel Temperature-Responsive Ionic Gel. 1. A Fast and Reversible Temperature Response in the Charge Density", J. Phys. Chem. B., 2004, pp. vol. 108, 16703-16707.
U.S. Application Publication No. 2013-0317172 A1.
Search report from International Application No. PCT/JP2011/079392, mail date is Mar. 19, 2012.
Search Report issued on Mar. 25, 2015 for EP 11848385.8.
Sakamoto C et al: "Temperature and pH-responsive aminopropyl-silica ion-exchange columns grafted with copolymers of N-isopropylacrylamide", Journal of Chromatography, vol. 1030, No. 1-2, Mar. 19, 2004, pp. 247-253.

* cited by examiner

Fig. 1

|  | Content of starting GMA mol% | Sulfonic acid group-containing monomer unit mol% | Elution amount of antibody by temperature change (A) mg/mL | Elution amount of antibody by a salt buffer (B) mg/mL | A/(A+B) × 100 % |
|---|---|---|---|---|---|
| Example 1 | 1 | 0.72 | 30.7 | 1.4 | 95.8 |
| Example 2 | 0.5 | 0.36 | 7.7 | 1.0 | 88.3 |
| Example 3 | 2 | 1.44 | 21.3 | 7.7 | 73.4 |
| Example 4 | 3 | 2.16 | 17.1 | 33.9 | 33.5 |
| Example 5 | 4 | 2.88 | 13.6 | 52.2 | 20.6 |
| Example 6 | 1 | 0.72 | 9.2 | 1.2 | 88.5 |
| Comparative Example 1 | 0 | 0 | 0.3 | 0.6 | 25.0 |
| Comparative Example 2 | 7 | 5.04 | 7.0 | 67.0 | 9.4 |

Fig. 2

| | Content of starting vinyl sulfonic acid mol% | Sulfonic acid group-containing monomer unit mol% | Elution amount of antibody by temperature change (A) mg/mL | Elution amount of antibody by a salt buffer (B) mg/mL | A/(A+B) × 100 % |
|---|---|---|---|---|---|
| Example 7 | 2 | 0.7 | 30.1 | 1.1 | 96.5 |

TEMPERATURE RESPONSIVE ADSORBENT HAVING A STRONG CATION EXCHANGE GROUP AND METHOD FOR PRODUCING THE SAME

The present application is a divisional of U.S. application Ser. No. 13/994,255, which is a National stags of International Patent Application No. PCT/JP2011/079392 filed Dec. 19, 2011, which claims priority to Japanese Application No. 2010-282373 filed Dec. 17, 2010. The disclosures of U.S. application Ser. No. 13/094,255 and International Patent Application No. PCT/JP2011/079392 are incorporated by reference herein in their entireties.

TECHNICAL FIELD

The present invention relates to a temperature responsive adsorbent in which the surface density of efficient cation exchange groups can be changed by temperature and a method for producing the same as well as a method for separating physiologically active substances serving as components of biomedicines by using the same.

BACKGROUND ART

An immunoglobulin (antibody) is a physiologically active substance responsible for an immune response. Recently, availability of immunoglobulin has been increased in applications such as medicines, diagnostic agents and separation/purification materials for the corresponding antigen protein. An antibody is taken from the blood of an immunized animal, a culture solution of a cell having antibody producibility or an ascitic fluid culture solution of the animal. However, such blood and a culture solution containing the antibody contain proteins other than the antibody or intricate contaminants derived from a raw-material solution used in the cell culture. Thus, to separate and purify the antibody from these impurity components, a complicated and time-consuming operation is usually required.

Liquid chromatography is important for separating and purifying an antibody. Examples of a chromatographic method for separating an antibody include gel filtration chromatography, affinity-chromatography, ion exchange chromatography and reverse phase chromatography. An antibody is separated and purified by a combination of these methods.

The ion exchange chromatography is a method of separating a counter ion present in a mobile phase by reversibly adsorbing it by an ion exchange group, which is present on the surface of an adsorbent and serves as a stationary phase. As the shape of the adsorbent, beads, flat film and a film such as a hollow fiber, are employed. These base materials, to which a cation exchange group or an anion exchange group is bound, are commercially available as adsorbents. The adsorbent having a cation exchange group, which has a property of mainly adsorbing an antibody and not adsorbing most of other contaminants, has a property of easily concentrating and separating an antibody.

Cation exchange groups are roughly divided into a weak cation exchange group such as a carboxyl group and a strong cation exchange group such as a sulfonic acid group. An adsorbent having a weak cation exchange group has a drawback in that the surface charge of the adsorbent changes as the pH of a mobile phase changes, with the result that a binding capacity to an antibody changes. Accordingly, if an adsorbent having a weak cation exchange group is used for separation/purification of an antibody, the reproducibility of separation becomes poor and the recovery rate of the antibody may decrease. In contrast, in an adsorbent having a strong cation exchange group, since the surface charge of the adsorbent does not change even if the pH of a mobile phase changes, the binding capacity to an antibody does not easily change. In industrial antibody separation/purification processes, although it is difficult to keep the pH of a mobile phase at a constant value, reproducibility of separation is stringently required. For this reason, an adsorbent having a strong cation exchange group is used.

In conventional adsorbents having an ion exchange group, a physiologically active substance adsorbed is generally eluted by increasing the salt concentration of a mobile phase. However, it is known that a physiologically active substance serving as a component of a biomedicine and the like may cause an irreversible change (denaturation) by changing a salt concentration (ion strength) of a mobile phase. Extreme care must be taken to determine these elution conditions. In addition, physiologically active substances are mostly separated and purified in sites (low-temperature chambers) controlled at low temperatures; however, when a physiologically active substance adsorbed is eluted in a mobile phase of a high salt-concentration, there is a risk that a salt precipitated at a low temperature causes clogging of a pipe and a column.

Then, to solve a problem of conventional adsorbents having an ion exchange group, a temperature responsive adsorbent is proposed, from which a physiologically active substance adsorbed can be eluted not by increasing the salt concentration of a mobile phase but by changing an efficient surface density of ion exchange group by temperature.

Patent Literature 1 discloses a packing material containing a charged copolymer, a method for producing the same and a temperature responsive chromatography using the same, in which an efficient surface charge density of a stationary phase can foe changed by temperature change. Patent Literature 2 discloses a temperature responsive chromatographic carrier prepared by densely immobilizing a polymer capable of changing hydration force within a temperature range of 0 to 80° C. to a base material surface by an atom transfer radical polymerization method. Patent Literature 3 discloses a method for producing a temperature responsive chromatographic carrier comprising growing a charged polymer capable of changing hydration force within a temperature range of 0 to 80° C. in accordance with a reaction of an atom transfer radical method using isopropyl alcohol as a solvent. Patent Literature 4 discloses a method for producing a liquid chromatographic carrier, which is prepared by covering a solid surface with a charged polymer capable of changing hydration force within a temperature range of 0 to 80° C., and which is capable of separating a high-molecular weight physiologically active substance useful in the fields of e.g., biology, medicine and pharmacy under specific conditions including an aqueous mobile phase. Non Patent Literature 1 discloses a temperature responsive chromatographic carrier having a carboxyl group and prepared by an atom transfer radical polymerization method and a process thereof. In the Literature, monomer compositions for use in an atom transfer radical polymerization method are disclosed including a monomer composition optimized for lysozyme separation.

CITATION LIST

Patent Literatures

Patent Literature 1: International Publication No. WO99/061904

Patent Literature 2: Japanese Patent Laid-Open No. 2007-69193

Patent Literature 3: Japanese Patent Laid-open No. 2009-85933

Patent Literature 4: International Publication No. WO01/074482

Non Patent Literatures

Non Patent Literature 1: Polymer Preprints, Japan Vol. 58, No. 2, 3T1-13 (2009)

SUMMARY OF INVENTION

Technical Problem

None of the aforementioned literatures disclose a temperature responsive adsorbent having a strong cation exchange group, of which surface is grafted with monomer compositions most suitable for purifying a protein such as an immunoglobulin, a method for producing the adsorbent and a method for applying the adsorbent. It is difficult to polymerize monomers having cation exchange group since they extremely reduce the reaction rate of surface graft polymerization. Because of this, the monomer has not yet been sufficiently studied. Then, an object of the present invention is to provide a temperature responsive adsorbent having an optimal ratio of a strong cation exchange group relative to N-isopropylacrylamide for purification of a protein such as an immunoglobulin by temperature change, and provide a method for producing the adsorbent and a method for applying the adsorbent.

Solution to Problem

The present inventors made research and development with a view of attaining the aforementioned object from various angles. As a result, the present inventors found that if a temperature responsive adsorbent is produced by a surface graft polymerization method using a reaction solution containing a monomer having a strong cation group such as sulfonic acid group or a precursor of a strong cation exchange group in a ratio of 0.01 to 5 mol % relative to N-isopropylacrylamide, the strong cation groups are immobilized to a base material surface at a suitable density for purifying a protein such as an immunoglobulin by temperature change. The technique disclosed in the present invention cannot be totally expected from the prior art and development toward a novel separation system of a physiologically active substance, which has never been exist in the prior art, is expected. The present invention was accomplished based on such a finding.

Advantageous Effects of Invention

Based on the temperature responsive adsorbent and methods for producing and applying the adsorbent described in the present invention, a novel separation system is proposed. If such a system is used, useful physiologically active substances such as proteins including immunoglobulins will be successfully separated/purified on an industrial scale by changing temperature.

BRIEF DESCRIPTION OF DRAWINGS

FIG. 1 shows a table summarizing experimental results of adsorption/elution tests of an antibody by the adsorbents prepared in Examples 1 to 6 and Comparative Examples 1 and 2.

FIG. 2 shows a table summarizing experimental results of an adsorption/elution test of an antibody by the adsorbent prepared in Example 7.

DESCRIPTION OF EMBODIMENTS

Preferred embodiment of the present invention (hereinafter, referred to as "the embodiment") will be described below in more detail. The temperature responsive adsorbent according to the embodiment is a temperature responsive adsorbent in which a copolymer containing at least N-isopropylacrylamide is immobilized to a base material surface. The copolymer has at least a strong cation exchange group. Furthermore, the copolymer contains the strong cation exchange group in an amount of 0.01 to 5 mol % in terms of monomer relative to N-isopropylacrylamide. The copolymer of the temperature responsive adsorbent according to the embodiment is, for example, formed by polymerizing monomer compositions, which contain monomer having the strong cation exchange group and/or precursor monomer for introducing the strong cation exchange group in a ratio of 0.01 to 5 mol % relative to N-isopropylacrylamide, by a surface graft polymerization method.

Examples of the shape of the base material to be used in the embodiment include, but are not particularly limited to, bead shape, flat-plate shape and tubular shape. In the case of the bead shape, beads having various particle sizes are available. Although it is not particularly limited, the particle size is satisfactorily 1 to 300 μm, preferably 10 to 200 μm and further preferably 20 to 150 μm. If the particle size is 1 μm or less, compaction of beads tends to occur in a column, with the result that treatment of the beads at a high flow rate tends to be difficult. In contrast, if the particle size is 300 μm or more, the space between beads increases, with the result that some of biopolymers tend to slip out in adsorbing them.

The base material to be used in the embodiment has, for example, a plurality of pores. Although it is not particularly limited, the pore diameter is satisfactorily 5 to 1000 nm, preferably 10 to 700 nm and further preferably 20 to 500 nm. If the pore diameter is 5 nm or less, the molecular weight of biopolymer to be separated tends to reduce. In contrast, if the pore diameter is 1000 nm or more, the surface area of the base material decreases, with the result that the binding capacity to a biopolymer tends to reduce.

In the embodiment, a temperature responsive polymer having the strong cation exchange group is immobilized to the above base material. Examples of the immobilization method include, but are not particularly limited to, an "atom transfer radical method" in which an atom transfer radical polymerization initiator is immobilized to a base material surface and a temperature responsive polymer is allowed to grow from the initiator through a reaction in the presence of a catalyst; and a "radiation graft polymerization method" in which a base material is irradiated with a radioactive ray to produce a radical and a temperature responsive polymer is allowed to grow through a reaction with the radical thus generated used as a starting point. Alternatively, as the immobilization method, a surface living radical polymerization method, i.e., "atom transfer radical polymerization method" is known. The "atom transfer radical polymerization method" can be suitably used since a polymer can be densely immobilized to a base material surface.

When the temperature responsive polymer is immobilized by the "atom transfer radical polymerization method", examples of the initiator to be used therein include, but are not particularly limited to, in the case where the base material has a hydroxy group as is in the embodiment, 1-trichlorosilyl-2-(m, p-chloromethylphenyl)ethane, 2-(4-chlorosulfonylphenyl)ethyl trimethoxysilane, (3-(2-bromoisobutyryl)propyl)dimethyl ethoxysilane and 2-bromoisobutyryl bromide. In the embodiment, a polymer chain grows from the initiator. Examples of a catalyst used therein include, but are not particularly limited to, copper halide ($Cu^I X$) such as $Cu^I Cl$ and $Cu^I Br$. Furthermore, examples of the ligand complex to the copper halide include, but are not particularly limited to, tris(2-(dimethylamino)ethyl)amine ($Me_6TREN$), N,N,N'',N''-pentamethyldiethylene triamine (PMDETA), 1,1,4,7,10,10-hexamethyltriethylene tetraamine (HMTETA), 1,4,8,11-tetramethyl 1,4,8,11-azacyclotetradecane ($Me_4Cyclam$) and bipyridine.

When the temperature responsive polymer is immobilized by the "radiation graft polymerization method", any means can be employed for generating radicals from the base material; however, to uniformly generate radicals from the whole base material, irradiation of ionizing radiation is preferable. Examples of the ionizing radiation include a γ ray, an electron beam, a β ray and a neutron beam. For irradiation of ionizing radiation on an industrial scale, an electron beam or a γ ray is preferable. Ionizing radiation can be obtained from a radioactive isotope such as cobalt 60, strontium 90 and cesium 137 or from an X-ray imager, an electron beam accelerator and a UV ray irradiation apparatus and others.

The irradiation dose of ionizing radiation is preferably 1 kGy or more and 1000 kGy or less, more preferably 2 kGy or more and 500 kGy or less and further preferably 5 kGy or more and 200 kGy or less. If the irradiation dose is less than 1 kGy, it tends to be difficult to generate radicals uniformly. In contrast, if the irradiation dose exceeds 1000 kGy, the physical strength of the base material tends to decrease.

Graft polymerization methods using irradiation of ionizing radiation are generally classified roughly into a pre-irradiation method, in which radicals are generated from a base material and then allowed to be in contact with a reactive compound, and a simultaneous irradiation method, in which radicals are generated from a base material while a film is allowed to be in contact with a reactive compound. In the embodiment, either method can be applied; however, a pre-irradiation method producing a small amount of oligomers is preferable.

In the embodiment, the solvent to be used in polymerization is not particularly limited as long as it can homogenously dissolve a reactive compound. As such a solvent, an alcohol such as ethanol, isopropanol and t-butyl alcohol; an ether such as diethyl ether and tetrahydrofuran, a ketone such as acetone and 2-butanone, water or a mixture of these is mentioned.

In the embodiment, the polymer to be used for covering the base material surface has N-isopropylacrylamide. Poly (N-isopropylacrylamide) is known to have a lower-limit critical temperature at 32° C. The carrier introduced into the surface of the polymer greatly changes surface physical properties such as hydrophilicity/hydrophobicity at a critical temperature. Therefore, if this is grafted or applied as a coating to the surface of a packing agent for chromatography, sample retentivity can be obtained depending upon the temperature. As a result, retention behavior can be controlled by temperature without changing the composition of an eluate. Control of the lower-limit critical temperature to be 32° C. or more can be made by copolymerizing a monomer, which is more hydrophilic than isopropylacrylamide, such as acrylamide, methacrylic acid, acrylic acid, dimethyl acrylamide and vinyl pyrrolidone, as a hydrophilic co-monomer, with N-isopropylacrylamide. Furthermore, control of the lower-limit critical temperature to be 32° C. or less can be made by copolymerizing a hydrophobic monomer such as styrene, an alkyl methacrylate and an alkyl acrylate, as a hydrophobic co-monomer, with N-isopropylacrylamide.

In the embodiment, the polymer for covering the base material surface has a strong cation exchange group such as a sulfonic acid group. As a method for providing a strong cation exchange group is not particularly limited. As a first method, there is a method in which a copolymerization is carried out such that a monomer having a strong cation exchange group is included to a copolymer when a temperature responsive polymer chain for covering a carrier surface is synthesized. Examples of a monomer unit having a sulfonic acid group include polymer component units having sulfonic acid such as (meth)acrylamide alkyl sulfonic acid, vinyl sulfonic acid, acrylamide t-butyl sulfonic acid and styrene sulfonic acid.

For example, in the case where at least a portion of monomer units of a copolymer is a moiety derived from a vinyl monomer having a sulfonic acid group, such as vinyl sulfonic acid, the sulfonic acid group binds to the main chain without the aid of a linker. For this, no hydrophobic interaction occurs between the linker and an antibody. As a result, when an antibody is eluted from the base material surface by temperature change, the elution amount by temperature change can be increased. Note that at least a portion of the monomer units of a copolymer having a strong cation exchange group can be represented by the following chemical formula (1):

$$—CR_1R_2—CR_3(—SO_3H)—  \quad (1)$$

where $R_1$, $R_2$, $R_3$ are each independently H or Me.

In the embodiment, as a second method for providing a strong cation exchange group to the polymer for covering the base material surface, there is a method comprising performing copolymerization of a monomer including a monomer having a "precursor for introducing a strong cation exchange group" and thereafter converting the precursor into the sulfonic acid group. Note that, the "precursor for introducing a strong cation exchange group" can include a "precursor of a strong cation exchange group". The "precursor of a strong cation exchange group" refers to, for example, a strong cation exchange group provided with a protecting group. As a monomer having a sulfonic acid group precursor, phenyl vinyl sulfonate and the like are mentioned but is not limited to these in the embodiment.

In the embodiment, as a third method for providing the strong cation exchange group to the polymer for covering the base material surface, there is a method comprising copolymerizing a monomer including a monomer having a functional group capable of providing a strong cation exchange group as a precursor monomer for introducing the strong cation exchange group, and thereafter converting the functional group capable of providing a strong cation exchange group into the sulfonic acid group. Examples of the monomer having a functional group capable of providing a strong cation exchange group include styrene and glycidyl methacrylate. In the case where a monomer having a strong cation exchange group is polymerized in accordance with a surface living radical polymerization method, a sufficient polymerization rate is not often obtained; however, if a precursor monomer for introducing a strong cation exchange group at least a part of which is a methacrylic acid derivative or an acrylic acid derivative such as glycidyl methacrylate is used, a sufficient polymerization rate can be obtained.

Furthermore, by virtue of the presence of a methacrylic acid derivative or an acrylic acid derivative as at least a portion of the monomer units of the copolymer having the strong cation exchange group, hydrophobic interaction between the base material or the other part of the copolymer and an antibody can be suppressed, increasing the elution amount of antibody in eluting the antibody from the base material surface by temperature change.

Furthermore, by virtue of the presence of a methacrylic acid derivative or an acrylic acid derivative as at least a portion of the monomer units of the copolymer having the strong cation exchange group, at least a portion of the monomer units of the copolymer having the strong cation exchange group has a group represented by the following chemical formula (2) or (3).

$$—CH(—OH)—CH_2—SO_3H \quad (2)$$

$$—CH(—SO_3H)—CH_2—OH \quad (3)$$

The sulfonic acid group of the monomer unit represented by the above chemical formula (2) binds to the main chain via a linker at least containing —CH(—OH)—CH$_2$—. Furthermore, the sulfonic acid group of the monomer unit represented by the above chemical formula (3) binds to the main chain via a linker at least containing —CH—. Since steric hindrance is suppressed by the linker, an antibody can quickly bind to the sulfonic acid group. Furthermore, the monomer units represented by the above chemical formulas (2) and (3) each have a hydroxy group in the proximity of a sulfonic acid group. By virtue of this, hydrophobic interaction between the base material or the other part of the copolymer and an antibody can be suppressed by the hydroxy group, increasing the elution amount of antibody in eluting the antibody from the base material surface by temperature change.

In the embodiment, the monomer composition having the monomer having the strong cation exchange group and/or the precursor monomer for introducing the strong cation exchange group in a ratio of 0.01 to 5 mol % relative to N-isopropylacrylamide is subjected to polymerization in accordance with the surface graft polymerization method. The above ratio is preferably 0.1 to 4 mol %, more preferably 0.2 to 3 mol %, further preferably 0.3 to 2 mol % and most preferably 0.5 to 1.5 mol %. If the above ratio exceeds 5 mol %, the amount of strong cation exchange group relative to the amount of N-isopropylacrylamide in the copolymer becomes excessive. As a result, the adsorption amount of immunoglobulin to the temperature responsive adsorbent increases; however most of the immunoglobulin adsorbed tends to be unsuccessfully eluted by temperature change. In contrast, if the above ratio is less than 0.01 mol %, the amount of strong cation exchange group to be introduced is excessively low. As a result, the adsorption amount of immunoglobulin itself tends to decrease.

In the embodiment, a copolymerization ratio (composition) of the monomer unit having the strong cation exchange group relative to N-isopropylacrylamide can be quantitatively determined by analyzing the copolymer immobilized to the base material surface. In analyzing the copolymerization ratio, various analysis approaches such as element analysis and NMR can be employed. Analyzing the copolymerization ratio after the copolymer is isolated from the base material is preferable in view of analysis accuracy since the effect of the base material upon analysis can be eliminated. If the copolymer cannot be isolated from the base material, the copolymer may be polymerized in a solution without using the base material. In this manner, the copolymer to be used for analysis of the copolymerization ratio can be obtained.

In the embodiment, the polymer covering the base material surface causes hydration and dehydration by changing temperature. The range of the temperature is 0° C. to 80° C., preferably, 5° C. to 50° C. and further preferably 10° C. to 45° C. If the temperature exceeds 80° C., e.g., vaporization occurs since the mobile phase consists of water, workability tends to decrease. In contrast, if the temperature is lower than 0° C., the mobile phase tends to freeze.

The temperature responsive adsorbent obtained by the embodiment is usually loaded to a liquid chromatographic apparatus and used as a liquid chromatography system. Although a method of applying temperature to a temperature responsive adsorbent in this case is not particularly limited, for example, loading the temperature responsive adsorbent in an aluminum block, a water bath, air layer or jacket adjusted to a predetermined temperature can be mentioned.

Although a separation method using the temperature responsive adsorbent according to the embodiment is not particularly limited; a method in which a desired biopolymer is once adsorbed to the temperature responsive liquid chromatographic carrier obtained and thereafter, the biopolymer adsorbed is released by changing temperature to thereby change characteristics of the carrier surface, in short, a method using a catch and release approach, is mentioned. The amount of solute to be adsorbed in this case may beyond or below the amount that the carrier can adsorb. Either method is a purification method of a solute by once adsorbing it and thereafter releasing it by changing temperature to thereby change the characteristics of the carrier surface.

Examples of other separation methods include, but are not particularly limited to, a method in which the temperature at which the characteristics of the carrier surface are changed is previously checked and impurities are separated by changing temperature with the predetermined temperature sandwiched in the middle. In this case, the characteristics of the carrier surface are greatly changed just by temperature change, and thus, the time until a signal appears (retention time) is expected to greatly differ depending upon the solute. In the case of the embodiment, the method is most effectively used if the solute is separated by changing temperature with the predetermined temperature, at which the characteristics of the carrier surface are greatly changed, sandwiched in the middle.

In the chromatography described in the embodiment, a buffer may be used as a mobile phase and no organic solvent is required. The buffer herein refers to an aqueous solution containing inorganic salts. Specific examples of the buffers include a phosphate buffer, a tris buffer and an acetic acid buffer. The buffer is not particularly limited as long as it is conventionally used. The concentration of the inorganic salts is satisfactorily 1 to 50 mmol/L, preferably 3 to 40 mmol/L and further preferably 5 to 30 mmol/L. If the concentration of inorganic salts in a mobile phase is lower than 1 mmol/L, the activity of a physiologically active substance serving as the solute tends to be inhibited. In addition, the dissociation degree of the ion exchange group on the temperature responsive adsorbent surface increases and the solute is tightly adsorbed to the temperature responsive adsorbent surface, with the result that removing the solute from the carrier surface by a subsequent operation tends to be difficult. Conversely, if the concentration of inorganic salts is higher than 50 mmol/L, the dissociation degree of the ion exchange group on the temperature responsive adsorbent surface decreases and the solute is rarely retained to a carrier surface. Finally, separating the solution tends to be difficult.

A neutral buffer to be used in the embodiment satisfactorily has a pH value of 4.0 to 7.5, preferably, 4.5 to 7.0 and further preferably 5.0 to 6.5. If the pH value of the buffer is higher than 7.5, an immunoglobulin (isoelectric point 7.5 to 10) is negatively charged and causes electrostatic repulsion to the strong cation exchange group that the temperature responsive adsorbent of the embodiment has, with the result that adsorption capacity tends to extremely decrease. Conversely, if a pH value is lower than 4.0, an immunoglobulin is denatured, with the result that quality loss such as reduction in activity and generation of aggregates tends to occur. In the embodiment, the protein is not particularly limited; however, since the embodiment is a separation method using the carrier surface having the strong cation exchange group, a basic protein is preferable. Specific examples of the basic protein include an immunoglobulin, lysozyme, hemoglobin β chain, catalase, annexin and ezrin. In particular, for purification of immunoglobulin, the separation method is preferably used.

If the temperature responsive adsorbent of the embodiment explained in the above is used, an extremely useful physiologically active substance for use in medicines, etc. can be separated and analyzed. In this case, separation can be made by a simple operation, i.e., just by changing the temperature within a column. In addition, since no organic solvent is required for separation, the physiologically active substance can be separated without being denatured.

Example 1

The embodiment will be more specifically described below based on examples; however, these examples should not be construed as limiting the embodiment.

In Example 1, a bead-shape temperature responsive adsorbent having a sulfonic acid group was synthesized by the atom transfer radical polymerization method.

1) Immobilization of Initiator

Crosslinked polyvinyl alcohol beads (1 g (particle size: 100 μm)) was moistened with pure water and placed in a 300-mL conical flask made of glass. To the conical flask, 200 mL of tetrahydrofuran (containing no stabilizer, manufactured by Kanto Chemical Co., Inc.), 1.23 mL of 2-bromoisobutyryl bromide (manufactured by Tokyo Chemical Industry Co., Ltd.) and 1.40 mL of triethylamine (manufactured by Wako Pure Chemical Industries Ltd.) were added and shaken at room temperature for 16 hours. After completion of the reaction, filtration was made and washing is performed three times with 200 mL of ethanol and storage was made in dehydrated isopropanol. In this manner, 2-bromoisobutyryl bromide serving as an atom transfer radical polymerization (ATRP) initiator was introduced into the surface of the crosslinked polyvinyl alcohol beads.

2) Surface Graft Polymerization

A monomer composition containing glycidyl methacrylate (GMA, manufactured by Tokyo Chemical Industry Co., Ltd.), which was a precursor monomer of a sulfonic acid group, in a ratio of 1 mol % relative to N-isopropylacrylamide was prepared. More specifically, 18.40 g of isopropylacrylamide (IPAAm, manufactured by Wako Pure Chemical Industries Ltd.), 0.231 g of GMA, 1.217 g of butyl methacrylate (BMA, manufactured by Tokyo Chemical Industry Co., Ltd.), 0.085 g of copper (I) chloride (CuCl, manufactured by Wako Pure Chemical Industries Ltd.), and 0.012 g of copper (II) chloride ($CuCl_2$, manufactured by Wako Pure Chemical Industries Ltd.) were dissolved in a 90 vol % aqueous isopropanol (IPA) solution (42.8 mL) and bubbled with nitrogen for 30 minutes. Thereafter, to the solution, 0.221 g of tris (2-dimethylaminoethyl)amine ($Me_6TREN$) (manufactured by Alfa Aesar) was added under a nitrogen atmosphere and the mixture was stirred for 5 minutes to form a catalyst of $CuCl/CuCl_2/Me_6TREN$. The reaction solution was reacted with an initiator-introduced crosslinked polyvinyl alcohol beads under a nitrogen atmosphere and subjected to ATRP at room temperature for 16 hours. After completion of the reaction, the monomer, polymer and copper catalyst were washed successively with ethanol, a 50 mmol/L-EDTA aqueous solution and pure water.

3) Introduction of a Sulfonic Acid Group

The graft-chain introduced beads by the atom transfer radical polymerization method were added to an aqueous solution (200 g) of a mixture of sodium sulfite and IPA (sodium sulfite/IPA/pure water=10/15/75 wt %) and reacted at 80° C. for 24 hours to convert an epoxy group in the graft chain into a sulfonic acid group. After completion of the reaction, the beads were washed with pure water. Thereafter, the beads were added to 0.5 mol/L sulfuric acid and reacted at 80° C. for 2 hours to convert the remaining epoxy group in the graft chain into a diol group. After completion of the reaction, the beads were washed with pure water.

4) Measurement of Copolymerization Ratio

Using a monomer composition containing glycidyl methacrylate (GMA, manufactured by Tokyo Chemical Industry Co., Ltd.), which was a precursor monomer of a sulfonic acid group, in a ratio of 1 mol % relative to N-isopropylacrylamide, a copolymer was polymerized without using a base material. More specifically, the reaction solution described in the above 2) was reacted with ethyl 2-bromoisobutyrate under a nitrogen atmosphere and subjected to ATRP at room temperature for 16 hours. After completion of the reaction, the reaction solution was poured in dialysis membrane (Spectra/por Dialysis Membrane, MWCO1000, manufactured by Spectrum Laboratories) and successively soaked in ethanol, a 50 mmol/L-EDTA aqueous solution and pure water to remove the monomer and the copper catalyst. Subsequently, the reaction solution was lyophilized. The resultant copolymer was added to an aqueous solution (200 g) of a mixture of sodium sulfite and IPA (sodium sulfite/IPA/pure water=10/15/75 wt %) and reacted at 80° C. for 24 hours to convert an epoxy group in the graft chain into a sulfonic acid group. After completion of the reaction, the reaction solution was poured in dialysis membrane and soaked in pure water to remove sodium sulfite and IPA. Subsequently, the reaction solution was lyophilized to obtain a copolymer.

The above copolymer (30 mg) was dissolved in heavy water (670 mg) and 1H-NMR was measured by a nuclear magnetic resonance apparatus (Bruker Avenve-600). Thereafter, based on the integrated value of a N-isopropylacrylamide unit-derived signal and the integrated value of a sulfonic acid group-derived signal, the copolymerization ratio (composition) of a monomer unit having a strong cation exchange group relative to N-isopropylacrylamide was calculated. As a result, the copolymerization ratio (composition) of the monomer unit having a strong cation exchange group relative to N-isopropylacrylamide was 0.72 mol %.

5) Measurement of Adsorption/Elution Amount of Immunoglobulin

A vacant column (Tricorn 5/20 column, manufactured by GS Healthcare Japan) was filled with the beads. The adsorption/elution test of an immunoglobulin (Venogloblin-IH blood donation, manufactured by Benesis Corporation) was performed by using a chromatography system (AKTA FPLC, manufactured by GE Healthcare Japan) by changing temperature. An operation for changing the temperature of the column filled with the beads was performed by temporarily stopping the pump of the chromatography system, soaking the column in a constant-temperature water vessel and thereafter storing it in a warm place for 10 minutes or more and driving the pump of the chromatography system, again. Adsorption and elution of an immunoglobulin were performed in the following conditions.

(Adsorption Step)
    An immunoglobulin concentration: 2.5 mg/mL
    Adsorption buffer: 15 mmol/L acetic acid buffer (pH 6.0)
    An immunoglobulin solution loading amount: 20 mL
    Flow rate: 0.4 mL/min
    Column volume: 0.54 ml
    Adsorption temperature: 40° C.

(Washing Step)
    Wash buffer: 15 mmol/L acetic acid buffer (pH 6.0)
    Flow rate: 0.4 mL/min
    Wash temperature: 40° C.

(Elution Step by Temperature Change)
    Elution buffer: 15 mmol/L acetic acid buffer (pH 6.0)
    Flow rate: 0.4 mL/min
    Flow amount: 20 mL
    Elution temperature: 2° C.

(Salt Elution Step)
    Elution buffer: 1 mol/L acetic acid buffer (pH 6.0)
    Flow rate: 0.4 mL/min
    Flow amount: 20 mL
    Elution temperature: 2° C.

After elution by temperature change, an immunoglobulin that cannot be completely eluted by temperature change was eluted with a 1 mol/L acetic acid buffer (pH 6.0). UV absorption (280 nm) in each step was measured and an immunoglobulin concentration was calculated in accordance with the following expression to obtain the elution amount of immunoglobulin by temperature change.

$$\text{Immunoglobulin concentration (mg/mL)} = \text{absorbance at 280 nm}/14 \times 10$$

$$\text{Elution amount by temperature change (mg/mL)} = \text{immunoglobulin concentration of fraction eluted by temperature change} \times \text{liquid amount of fraction eluted by temperature change}/\text{column volume}$$

(Results)

As shown in FIG. 1, the elution amount of immunoglobulin by temperature change is 30.7 mg/mL, demonstrating that the immunoglobulin can be eluted by temperature change. After elution by temperature change, the immunoglobulin left on the beads was eluted by a salt buffer. As a result, the elution amount by the salt buffer was as low as 1.4 mg/mL. From the above results, it was demonstrated that the temperature responsive adsorbent can be used for industrial immunoglobulin purification.

Example 2

In a surface graft polymerization reaction, a monomer composition containing glycidyl methacrylate, which was a precursor monomer of a sulfonic acid group, in a ratio of 0.5 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), glycidyl methacrylate (0.116 g), butyl methacrylate (1.217 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1. Furthermore, a copolymerization ratio was determined in the same manner as in Example 1 except that the reaction solution having the above composition was used. As a result, the copolymerization ratio (composition) of the monomer unit having the strong cation exchange group relative to N-isopropylacrylamide was 0.36 mol %.

(Results)

As shown in FIG. 1, the elusion amount of immunoglobulin by temperature change was 7.7 mg/mL, demonstrating that the immunoglobulin can be eluted by temperature change. After elution by temperature change, the immunoglobulin left on the beads was eluted by a salt buffer. As a result, the elution amount by the salt buffer was as low as 1.0 mg/mL. From the above results, it was demonstrated that the temperature responsive adsorbent can be used for industrial immunoglobulin purification.

Example 3

In a surface graft polymerization reaction, a monomer composition containing glycidyl methacrylate, which was a precursor monomer of a sulfonic acid group, in a ratio of 2 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), glycidyl methacrylate (0.462 g)butyl methacrylate (1.217 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1. Furthermore, a copolymerization ratio was determined in the same manner as in Example 1 except that the reaction solution having the above composition was used. As a result, the copolymerization ratio (composition) of the monomer unit having the strong cation exchange group relative to N-isopropylacrylamide was 1.44 mol %.

(Results)

As shown in FIG. 1, the elusion amount of immunoglobulin by temperature change was 21.3 mg/mL, demonstrating that the immunoglobulin can be eluted by temperature change. After elution by temperature change, the immunoglobulin left on the beads was eluted by a salt buffer. As a result, the elution amount by the salt buffer was as low as 7.7 mg/mL. From the above results, it was demonstrated that the temperature responsive adsorbent can be used for industrial immunoglobulin purification.

Example 4

In a surface graft polymerization reaction, a monomer composition containing glycidyl methacrylate, which was a precursor monomer of a sulfonic acid group, in a ratio of 3 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), glycidyl methacrylate (0.694 g), butyl methacrylate (1.21 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1. Furthermore, a copolymerization ratio was determined in the same manner as in Example 1 except that the reaction solution having the above composition was used. As a result, the copolymerization ratio (composition) of the monomer unit having the strong cation exchange group relative to N-isopropylacrylamide was 2.16 mol %.
(Results)

As shown in FIG. 1, the elusion amount of immunoglobulin by temperature change was 17.1 mg/mL, demonstrating that the immunoglobulin can be eluted by temperature change. After elution by temperature change, the immunoglobulin left on the beads was eluted by a salt buffer. As a result, the elution amount by the salt buffer was 33.9 mg/mL. From the above results, it was demonstrated that the temperature responsive adsorbent can be used for industrial immunoglobulin purification.

Example 5

In a surface graft polymerization reaction, a monomer composition containing glycidyl methacrylate, which was a precursor monomer of a sulfonic acid group, in a ratio of 4 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), glycidyl methacrylate (0.924 g), butyl methacrylate (1.217 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1. Furthermore, a copolymerization ratio was determined in the same manner as in Example 1 except that the reaction solution having the above composition was used. As a result, the copolymerization ratio (composition) of the monomer unit having the strong cation exchange group relative to N-isopropylacrylamide was 2.88 mol %.
(Results)

As shown in FIG. 1, the elusion amount of immunoglobulin by temperature change was 13.6 mg/mL, demonstrating that the immunoglobulin can be eluted by temperature change. After elution by temperature change, the immunoglobulin left on the beads was eluted by a salt buffer. As a result, the elution amount by the salt buffer was 52.2 mg/mL. From the above results, it was demonstrated that the temperature responsive adsorbent can be used for industrial immunoglobulin purification.

Example 6

A hollow fiber shape temperature responsive adsorbent having a sulfonic acid group was synthesized in accordance with a γ ray graft polymerization method.
1) Surface Graft Polymerization N-isopropylacrylamide (4.66 g), glycidyl methacrylate (0.059 g) and butyl methacrylate (0.120 g) were dissolved in a 25 vol % aqueous t-butanol solution (200 mL) and bubbled with nitrogen for 30 minutes. This was used as a reaction solution. Polyethylene hollow fiber (0.800 g (10 cm, 4 filaments), inner diameter: 2.0 mm, outer diameter: 3.0 mm, average pore diameter: 0.25 μm,) was cooled with dry ice to −60° C. under a nitrogen atmosphere, and irradiated with γ rays at 35 kGy using Co60 as a radiation source. The hollow fiber irradiated was allowed to stand still under a reduced pressure of 13.4 Pa or less for 5 minutes and thereafter contacted with the above reaction solution (20 mL) at 40° C. and allowed to stand still for 16 hours. Thereafter, the hollow fiber was washed with ethanol and dried in a vacuum dryer.
2) Introduction of Sulfonic Acid Group The hollow fiber having a graft chain introduced therein by the γ ray graft polymerization method was placed in an aqueous solution (500 g) of a mixture of sodium sulfite and IPA (sodium sulfite/IPA/pure water=10/15/75 wt %) and reacted at 80° C. for 24 hours to convert an epoxy group in the graft chain into a sulfonic acid group. After completion of the reaction, the hollow fiber was washed with pure water. Thereafter, the hollow fiber was added to 0.5 mol/L sulfuric acid and reacted at 80° C. for 2 hours to convert the remaining epoxy group in the graft chain into a dial group. After completion of the reaction, the hollow fiber was washed with pure water, and a film was washed with ethanol and dried in a vacuum drier.
3) Measurement of Adsorption/Elution Amount of Immunoglobulin The hollow fiber (film volume: 0.5 mL) modularized was subjected to an adsorption/elution test of an immunoglobulin (Venogloblin-IH blood donation, manufactured by Benesis Corporation) using a chromatography system (AKTA FPLC, manufactured by GE Healthcare Japan) by temperature change. An operation for changing the temperature of the hollow fiber module was performed by temporarily stopping the pump of the chromatography system, soaking the hollow fiber module in a constant-temperature water vessel, and thereafter storing it in a warm place for 10 minutes or more, and driving the pump of the chromatography system, again. Adsorption and elution of an immunoglobulin were performed in the following conditions.
(Adsorption Step)

An immunoglobulin concentration: 2.5 mg/mL

Adsorption buffer: 15 mmol/L acetic acid buffer (pH 6.0)

An immunoglobulin solution loading amount: 20 mL

Flow rate: 0.4 mL/min

Column volume: 0.54 mL

Adsorption temperature: 40° C.
(Washing Step)

Wash buffer: 15 mmol/L acetic acid buffer (pH 6.0)

Flow rate: 0.4 mL/min
(Elution Step by Temperature Change)

Elution buffer: 15 mmol/L acetic acid buffer (pH 6.0)

Flow rate: 0.4 mL/min

Amount of liquid passed through: 20 mL

Elution temperature: 2° C.
(Salt Elution Step)

Elution buffer: 1 mol/L acetic acid buffer (pH 6.0)

Flow rate: 0.4 mL/min

Amount of liquid passed through: 20 mL

Elution temperature: 2° C.

After elution by temperature change, an immunoglobulin that cannot be completely eluted by temperature change was eluted with a 1 mol/L acetic acid buffer (pH 6.0). UV absorption (280 nm) of fractions in each step was measured and an immunoglobulin concentration was calculated in accordance with the following expression to obtain the elution amount of immunoglobulin by temperature change.

An immunoglobulin concentration (mg/mL)=absorbance at 280 nm/14×10

Elution amount by temperature change (mg/mL)=immunoglobulin concentration of fraction eluted by temperature change×liquid amount of fraction eluted by temperature change/film volume Furthermore, a copolymerization ratio was determined in the same manner as in Example 1 except that the reaction solution having the composition prepared above, was used. As a result, the copolymerization ratio (composition) of the monomer unit having the strong cation exchange group relative to N-isopropylacrylamide was 0.72 mol %.
(Results)

As shown in FIG. 1, the elusion amount of immunoglobulin by temperature change was 9.2 mg/mL, demonstrating that an immunoglobulin can be eluted by temperature change. After elution by temperature change, the immunoglobulin left on the hollow fiber was eluted by a salt buffer. As a result, the elution amount by the salt buffer was as low as 1.2 mg/mL. From the above results, it was demonstrated that the temperature responsive adsorbent can be used for industrial immunoglobulin purification.

Example 7

1) Immobilization of Initiator

Crosslinked polyvinyl alcohol beads (1 g (particle size: 100 μm)) were moistened with pure water and placed in a 300-mL conical flask made of glass. To the conical flask, a 3% aqueous sodium hydroxide solution (150 mL) and epichlorohydrin (50 g) were added and stirred at 30° C. for 2 hours. After completion of the reaction, filtration was performed and washing was made five times with pure water (200 mL). To the beads, 100 mL of a 25% aqueous ammonia solution was added and stirred at 50° C. for 2 hours. After completion of the reaction, filtration was performed and washing was made five times with pure water (200 mL). Furthermore, to the beads, 1.75 g of 4,4-azobis(4-cyanovaleric acid) (ACV), 3.00 g of 1-ethoxycarbonyl-2-ethoxy-1,2dihydroquinone (EEDQ) and 80 mL of dimethylformamide were added and stirred at 25° C. for 24 hours. After completion of the reaction, filtration was performed and washing was made five times with pure water (200 mL).

2) Surface Graft Polymerization

A monomer composition containing vinyl sulfonic acid (manufactured by ASAHI KASEI FINECHEM CO., LTD.), which was a sulfonic acid group containing monomer, in a ratio of 2 mol % relative to N-isopropylacrylamide was prepared. More specifically, 4.66 g of H-isopropylacrylamide, 0.09 g of vinyl sulfonic acid and 0.12 g of butyl methacrylate were dissolved in t-butyl alcohol (42.8 mL) and bubbled with nitrogen for 30 minutes. The reaction solution was reacted with a crosslinked polyvinyl alcohol beads having an initiator introduced therein under a nitrogen atmosphere and the reaction was performed at 70° C. for 16 hours. After completion of the reaction, the monomer, polymer was washed successively with ethanol and pure water.

3) Measurement of Copolymerization Ratio

Using a monomer composition containing vinyl sulfonic acid, which was a sulfonic acid group containing monomer, in a ratio of 2 mol % relative to N-isopropylacrylamide, a copolymer was polymerized without using a base material. More specifically, the reaction solution described in the above 2) was reacted with ACV under a nitrogen atmosphere at 70° C. for 16 hours. After completion of the reaction, the reaction solution was poured in dialysis membrane (Spectra/por Dialysis Membrane, MWCO1000, manufactured by Spectrum Laboratories) and successively soaked in ethanol and pure water to remove the monomer. Subsequently, the reaction solution was lyophilized to obtain the copolymer.

The above copolymer (30 mg) was dissolved in heavy water (670 mg) and 1H-NMR was measured by a nuclear magnetic resonance apparatus (Bruker Avenve-600). Thereafter, based on the integrated value of a N-isopropylacrylamide unit-derived signal and the integrated value of a sulfonic acid group-derived signal, the copolymerization ratio (composition) of the monomer unit having the strong cation exchange group relative to N-isopropylacrylamide was calculated. As a result, the copolymerization ratio (composition) of the monomer unit having the strong cation exchange group relative to N-isopropylacrylamide was 0.70 mol %.
(Test and Results)

An adsorption and elution test of an immunoglobulin was performed in the same manner as in Example 1. As shown in FIG. 2, the elusion amount of immunoglobulin by temperature change was 30.1 mg/mL, demonstrating that the immunoglobulin can be eluted by temperature change. After elution by temperature change, the immunoglobulin left on the beads was eluted by a salt buffer. As a result, the elution amount by the salt buffer was 1.1 mg/mL. From the above results, it was demonstrated that the temperature responsive adsorbent can be used for industrial immunoglobulin purification.

Comparative Example 1

In a surface graft polymerization reaction, a monomer composition containing glycidyl methacrylate, which was a precursor monomer of a sulfonic acid group, in a ratio of 0 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), butyl methacrylate (1.217 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1.
(Results)

As shown in FIG. 1, the elusion amount of immunoglobulin by temperature change was 0.3 mg/mL. After elution by temperature change, the immunoglobulin left on the beads was eluted by a salt buffer. As a result, the elution amount by the salt buffer was 0.6 mg/mL.

Comparative Example 2

In a surface graft polymerization reaction, a monomer composition containing glycidyl methacrylate, which was a precursor monomer of a sulfonic acid group, in a ratio of 7 mol % relative to N-isopropylacrylamide was prepared and put in use. More specifically, a temperature responsive adsorbent was synthesized in the same manner as in Example 1 except that a reaction solution prepared by dissolving N-isopropylacrylamide (18.40 g), glycidyl methacrylate (1.618 g), butyl methacrylate (1.217 g), copper I chloride (0.085 g) and copper (II) chloride (0.012 g) in a 90 vol % aqueous isopropanol (IPA) solution (42.8 mL) was used, and an adsorption and elution test of an immunoglobulin was performed in the same manner as in Example 1. Furthermore, a copolymerization ratio was determined in the same manner as in Example 1 except that the reaction solution having the above composition was used. As a result, the copolymerization ratio (composition) of the monomer unit having the strong cation exchange group relative to N-isopropylacrylamide was 5.04 mol %.

(Results)

As shown in FIG. 1, the elusion amount of immunoglobulin by temperature change was 7.0 mg/mL. After elution by temperature change, the immunoglobulin left on the beads was eluted by a salt buffer. As a result, the elution amount by the salt buffer was 67.0 mg/mL.

The present application was made based on Japanese Patent Application (Japanese Patent Application No. 2010-282373) filed on Dec. 17, 2010 with the Japanese Patent Office and the content thereof is incorporated by reference.

INDUSTRIAL APPLICABILITY

A novel separation system is proposed based on the temperature responsive adsorbent according to the embodiment, a production method for the adsorbent and an application method for the adsorbent. If this system is used, useful physiologically active compounds such as globulins can be fractionated by temperature change on an industrial scale.

The invention claimed is:

1. A temperature responsive adsorbent capable of separating a physiologically active substance comprising a copolymer containing at least N-isopropylacrylamide immobilized to a support material surface, wherein at least a portion of monomer units of the copolymer has a sulfonic acid group, and the sulfonic acid group is introduced into the copolymer by polymerizing monomer compositions by a surface graft polymerization method to form the copolymer, each of the monomer compositions containing a monomer having the sulfonic acid group and/or a precursor monomer for introducing the sulfonic acid group in a ratio of 0.01 to 5 mol % relative to the N-isopropylacrylamide, wherein at least a portion of the monomer units of the copolymer having the sulfonic acid group is an acrylic acid derivative or a methacrylic acid derivative and has a group represented by the following chemical formula (4) or (5):

$$—CH(—OH)—CH_2—SO_3H \quad (4)$$

$$—CH(—SO_3H)—CH_2—OH \quad (5).$$

2. The temperature responsive adsorbent according to claim 1, wherein at least a portion of the precursor monomers for introducing the sulfonic acid group is an acrylic acid derivative or a methacrylic acid derivative and has a group represented by the chemical formula (4) or (5).

3. The temperature responsive adsorbent according to claim 1, wherein the surface graft polymerization method is a surface living radical polymerization method.

4. The temperature responsive adsorbent according to claim 1, wherein the surface graft polymerization method is a radiation radical polymerization method.

5. A temperature responsive adsorbent capable of separating a physiologically active substance comprising a copolymer containing at least N-isopropylacrylamide immobilized to a support material surface, wherein at least a portion of monomer units of the copolymer has a sulfonic acid group, and the sulfonic acid group is introduced into the copolymer by polymerizing monomer compositions by a surface graft polymerization method to form the copolymer, each of the monomer compositions containing a monomer having the sulfonic acid group and/or a precursor monomer for introducing the sulfonic acid group in a ratio of 0.01 to 5 mol % relative to the N-isopropylacrylamide, wherein at least a portion of the monomer units of the copolymer having the sulfonic acid group is derived from a vinyl monomer having a sulfonic acid group.

6. The temperature responsive adsorbent according to claim 5, wherein at least a portion of the monomers having the sulfonic acid group is a vinyl monomer having a sulfonic acid group.

7. The temperature responsive adsorbent according to claim 5, wherein at least a portion of the monomer units of the copolymer having the sulfonic acid group is represented by the following chemical formula (8):

$$—CR_1R_2—CR_3(—SO_3H)— \quad (8)$$

where $R_1$, $R_2$, and $R_3$ each is independently H or Me.

* * * * *